(12) United States Patent
Spruth et al.

(10) Patent No.: US 8,248,088 B2
(45) Date of Patent: Aug. 21, 2012

(54) REMOTE MONITOR FOR CORROSION PROTECTION OF PIPELINES AND STRUCTURES

(76) Inventors: John Murray Spruth, Houston, TX (US); Daniel Jay Schacht, Houston, TX (US)

( * ) Notice: Subject to any disclaimer, the term of this patent is extended or adjusted under 35 U.S.C. 154(b) by 300 days.

(21) Appl. No.: 12/701,940

(22) Filed: Feb. 8, 2010

(65) Prior Publication Data

US 2011/0193577 A1 Aug. 11, 2011

(51) Int. Cl.
  *G01R 27/08* (2006.01)
  *G01N 27/00* (2006.01)
(52) U.S. Cl. .................. 324/700; 324/71.2
(58) Field of Classification Search .......... 324/700, 324/699, 693, 691, 649, 600, 713, 522, 71.1, 324/512, 71.2, 76.11; 204/400, 404; 205/647, 205/640, 775.5; 73/86
See application file for complete search history.

(56) References Cited

U.S. PATENT DOCUMENTS

| 4,843,319 | A | * | 6/1989 | Lara ........................... 324/240 |
| 4,947,132 | A | * | 8/1990 | Charoy et al. ............... 324/699 |
| 6,965,320 | B1 | * | 11/2005 | Casey et al. ............. 340/870.07 |
| 7,034,553 | B2 | * | 4/2006 | Gilboe ......................... 324/700 |
| 7,088,115 | B1 | * | 8/2006 | Glenn et al. .................. 324/691 |
| 7,317,321 | B2 | * | 1/2008 | Hilleary ....................... 324/700 |
| 7,633,302 | B2 | * | 12/2009 | Peters ......................... 324/700 |
| 7,884,626 | B2 | * | 2/2011 | Peters ......................... 324/700 |

* cited by examiner

Primary Examiner — Hoai-An D Nguyen

(57) ABSTRACT

Several remote monitoring stations along a corrosion protected pipeline or structure are served by a single long range radio transceiver link to a central data collection station. Individual monitoring stations are in cost-free, short range communication with each other, while a single central module has an additional longer range, paid subscriber transceiver. The number of paid subscription links by cellular or satellite services to remotely monitor corrosion protection voltages and currents are substantially lessened by this combination.

5 Claims, 4 Drawing Sheets

REMOTE MONITOR FOR CORROSION PROTECTION OF PIPELINES AND STRUCTURES

OVERVIEW OF THE INVENTION

A protective DC source, known to the art, has a transformer and diode bridge to provide a DC protective voltage of negative polarity to a metal structure such as a pipeline. Although the pipe is coated with external insulation, breaches or 'holidays' in the insulation serve as areas for metallic corrosion and potential pipeline failure. This erosion of the exposed metal is also known as electrolytic corrosion. At distance intervals of 1 to 3 miles buried along the pipeline, active coupons made from the same alloy as the pipeline are attached through a surface junction box to the pipe metal with insulated wire. These active coupons act as surrogates for pipe holidays. Depending upon soil conditions, an active coupon would corrode without the protective DC source. The active coupon is buried in the same soil near the buried pipe with an insulated wire brought to the surface junction box. Measurements are taken at each junction box by walking the line with a hand-held meter or data-recording device. This is a labor-intensive and sometimes hazardous task to collect data on a pipeline. The hand held apparatus to remotely measure the protective voltage is herein known as a Hand Held Corrosion Protection Monitor (HHCPM). The HHCPM is manually carried to each surface junction box to report the condition at each distant point to alert the operator of the DC protective source, commonly known as a rectifier, to raise or lower the rectifier voltage accordingly.

OUTLINE OF THE INVENTION

The apparatus herein described removes the need to walk the pipeline to obtain timely and relevant data on the corrosion protection applied to the pipe. This apparatus is referred to here as a Remote CPM station, or RCPM, having a number of features to monitor each pipeline inspection site without the need for the physical presence of field personnel. At each inspection site, located at periodic distances, a self-powered data module will monitor a number of parameters of interest to the corrosion protection industry. These values include but are not limited to the DC potential between the active coupon and a reference electrode, the DC decay potential upon temporarily disconnecting the active coupon from the pipe, the AC potential between the reference electrode and the active coupon under the connected and disconnected conditions, the DC and AC currents flowing between the active coupon and the reference electrode, stray electrical fields induced on the pipeline by nearby power transmission systems, electrical rail systems, other nearby pipelines, etc. Automatic measurements of the potential on a native coupon that is not connected to the pipe are also taken.

These and other useful measurements are switched to a number of gain controlled amplifiers with mechanical relay contacts and solid-state analog switches. These amplifiers supply their output values to a supervisory microprocessor unit, MPU having at least one analog to digital A/D converter input. The gain of each amplifier is under the control of the MPU. Individual readings are cycled through by the MPU software and stored for retrieval as a digital value within the MPU or external memory storage. Between readings, the MPU enters a sleep state to preserve power requirements. A real time clock RTC contained in the MPU wakes the circuit for readings and remote data transmission. Additionally, out of bound conditions caused by a loss of DC current or too little or too much voltage on the pipeline results in an alarm condition which wakes the MPU for immediate data transmission. The MPU is also alerted to awake and process data or change program parameters upon receipt of an external wireless signal.

Periodically, the MPU awakens and reads all desired values into storage memory. These values are then transmitted by means of a short range transceiver SRT to a nearby remote station or to a more distant data reception point by means of a cellular service transceiver CST or orbiting satellite transceiver OST.

A number of RCPMs having only SRTs along a stretch of the pipeline are in communication with and will relay the data of each station to the next station. Every few stations, a base station having both a SRT and CST will relay data to a cellular tower transceiver. In remote regions, beyond cellular contact, the base station is equipped with a SRT and an OST.

The data block is confined to a short burst of information having a header containing a date and time stamp, a unit number, and digitally encoded measured values. This information is collected at a central office terminal COT.

The fact that the RCPM requires unattended observation of a protected structure and alerts a distant station offers great cost savings.

DETAILED DESCRIPTION OF THE DRAWINGS

Figure 1:
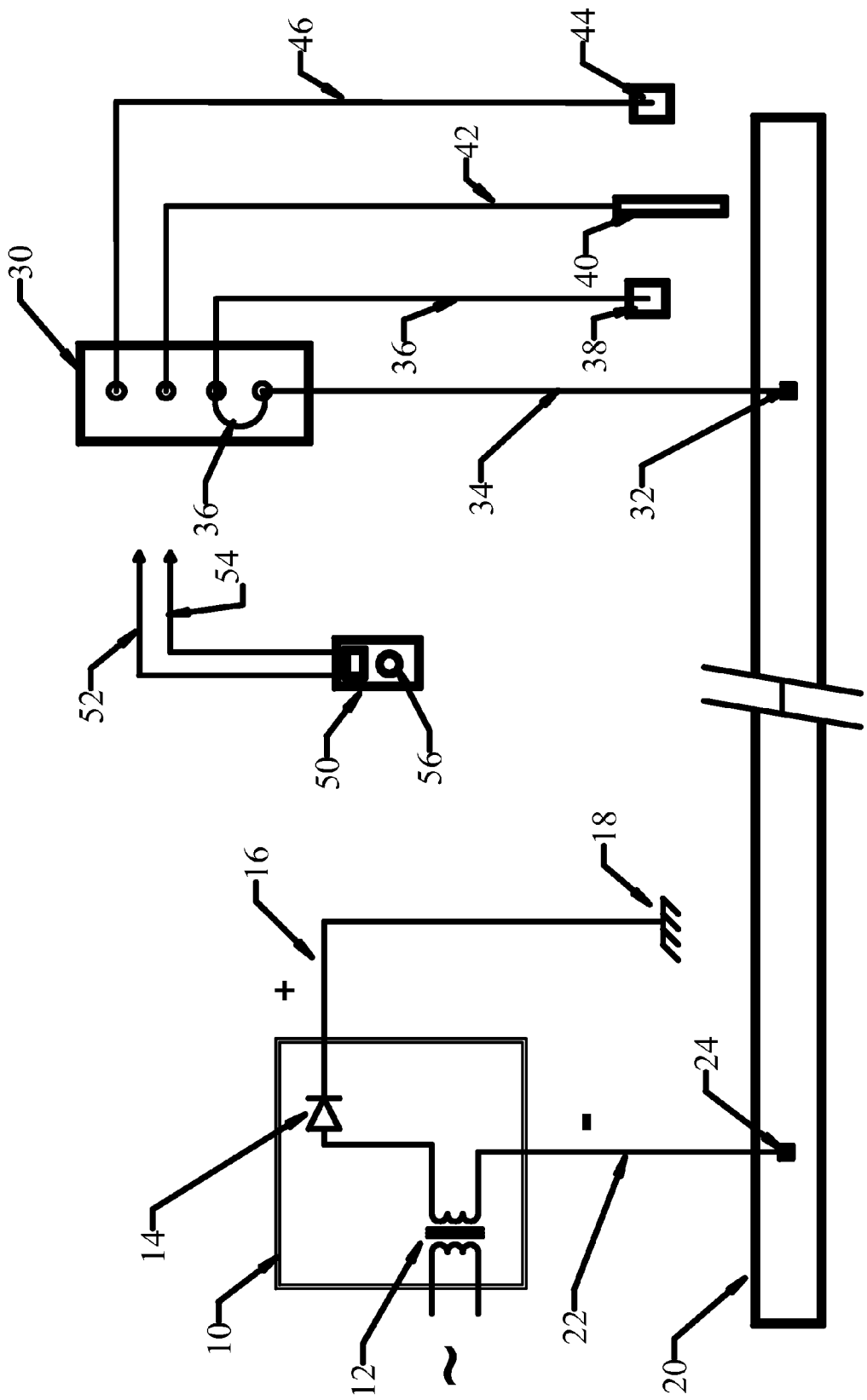
FIG. 1 is an schematic of the prior art manual apparatus.

FIG. 1 is a schematic drawing of the prior art showing a rectifier 10 with a typical AC transformer 12 and diode 14 producing a protective DC voltage at sufficient DC current. The positive output line 16 is connected to an anode bed 18 buried below grade in the ground. The anode bed can be any large enough mass of bare metal directly exposed to the surrounding soil. The negative output is electrically connected by line 22 to the pipe 20 at connector 24. A good connection is made to a bare patch on the pipe at connector 24 and covered over with an insulated patch. Lines 16 and 22 are insulated from the ground in order to convey the DC current only to the anode bed and the pipe or other structure to be protected.

At some distance from the rectifier, a test station 30 is connected by insulated wire 34 to a pipe connection 32. The connection 32 is covered over with an insulated patch to prevent any current flow into the surrounding soil at this point. The test station 30 is located above grade and internal terminals are accessible for measurements taken with a hand held meter 50 with measuring leads 52 and 54. A selector dial 56 allows the manual selection of various electrical readings.

Buried near the pipe in the same soil as the pipe is an active coupon 38 made from the same alloy as the pipe. This coupon can be a small cylinder of pipe alloy with a known bare area in contact with the soil. An insulated wire 36 is brought above grade to a terminal in the test station. A removable jumper or normally closed switch 36 completes the electrical connection from the active coupon to the pipe. Active coupon 38 is a surrogate for a bare spot on the pipe.

An electrochemical half-cell, known as a reference electrode 40 is buried a known distance away from the active coupon 38. This reference electrode is usually a hollow cylinder filled with moist copper sulfate crystals and contacted with the soil by a porous plug of ceramic. This reference electrode is coupled electrically to a terminal in the test station by insulated wire 42. A native coupon 44 is connected by insulated wire 46 to another terminal in the test station. The native coupon is not connected to the pipe and serves to provide a corrosion reference showing the effects of the soil on the unprotected pipe alloy.

Figure 2:
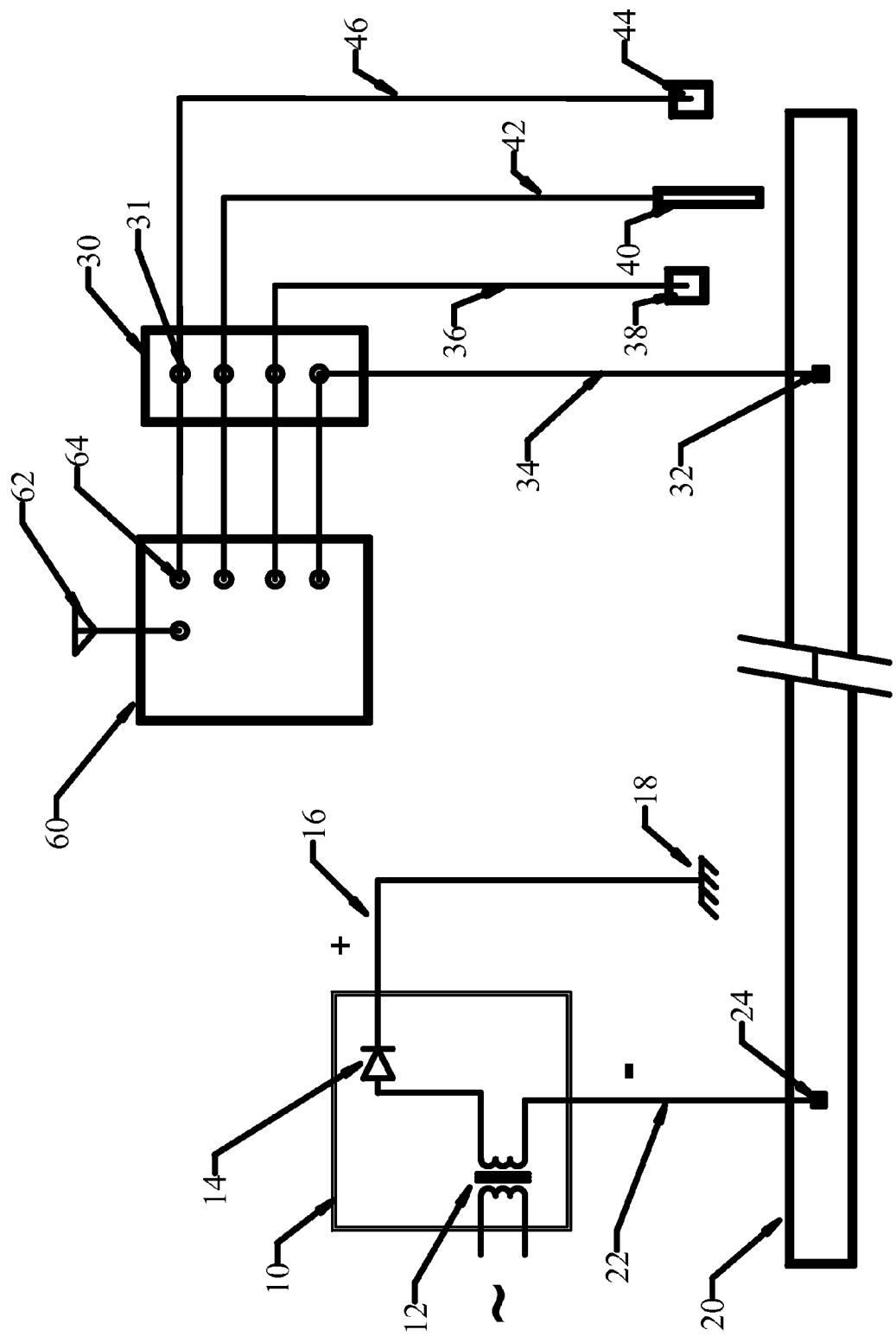
FIG. 2 is a schematic view of the external data collector and transceiver circuits.

In this application, FIG. 2 replaces the Hand held meter with a permanently installed data module 60 connected to the test station. Most test stations are constructed as a single hollow post of approximately 10 cm (4") in internal diameter that easily accommodates data module 60 and connects terminals 64 to the individual terminals 31 of test station 30. Data module 60 bidirectionally communicates data with at least one internal wireless transceiver connected to a multiband antenna 62.

Figure 3:
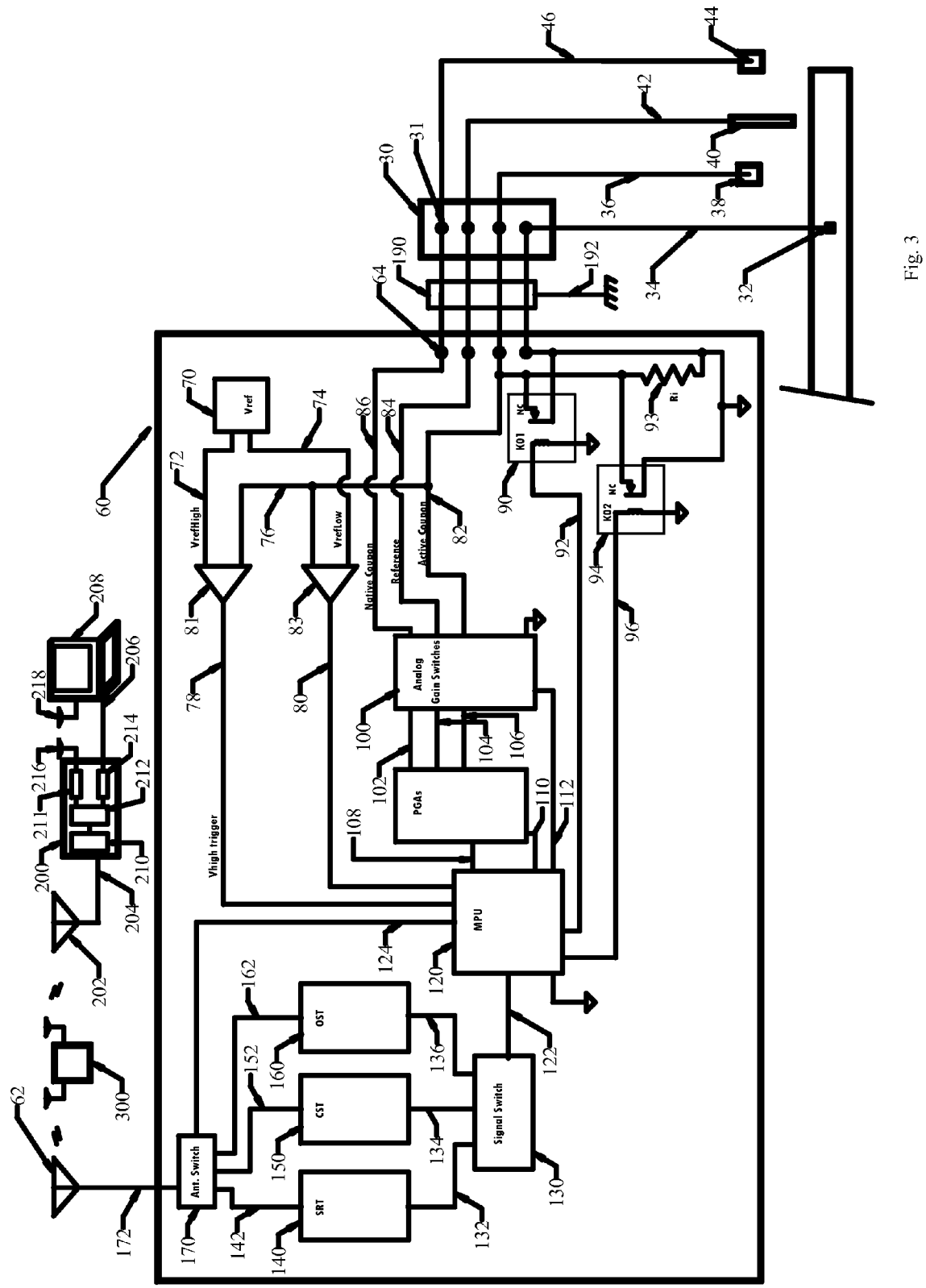
FIG. 3 is a detailed schematic of data collection circuit.

In this application, FIG. 3 details the overall circuitry of the data module 60. Starting at the right of data module 60, a protection array 190 contains components arranged to protect against high voltage surges on the pipe caused by lightning, and over-currents caused by accidental shorts to the pipe from external sources. Terminal lead 192 shunts any surge to earth ground without compromising the input signals. Data module terminals 64 bring the independent signals from the native coupon 44 through conductive lead 86, reference electrode 40 through conductive lead 84, and active coupon 38 through conductive lead 82 to analog gain switching circuits 100. A pair of comparators 81 and 83 monitor an upper voltage threshold and a lower voltage threshold between the reference electrode 40 and the active coupon 38. A stable voltage reference circuit 70 provides an upper trip level 72 and a lower trip level 74 to comparators 81 and 83 respectively. Outputs from the upper limit comparator 81 and lower limit comparator 83 are conveyed to the multi-processing unit [MPU] 120 via conductive leads 78 and 80 respectively. The MPU 120 treats these signals as digital warning levels. As long as the voltage between the reference and the active coupon is within the acceptable range, the MPU remains in a passive, non-alarmed state.

Relays 90 and 94 are temporarily activated relays to open normally-closed isolated contacts to alter the flow of measurable signals from terminals 64. A useful measurement to determine the actual voltage on the pipeline and ignore the voltage drop through the resistive earth surrounding the buried pipe is obtained by opening relay 90 contacts and measuring the voltage decay curve between the active coupon and the reference electrode. Several measurements are taken at intervals of time and recorded within the MPU memory.

Another useful measurement of the current flowing to the active coupon is obtained by measuring the voltage across a known standard resistor Ri 93. By Ohm's Law, the current will be proportion to the voltage measured across the resistor. Choosing resistor Ri 93 to be 1 ohm (for example) results in a one-to-one ratio between the voltage and the current. Since each coupon has a standard exposed area, the current per unit area is being measured. Relay 94 normally shorts out Ri 93. Upon receiving a command from MPU 120 along conductive lead 96, the relay is energized to open the relay contacts to take this measurement.

Since one cannot predict in advance what voltages may be present on a pipeline, including those from external sources including induced AC voltages from nearby power lines, the input voltages are scaled from the native coupon, the reference, and the active coupon through a series of analog gain switches 100 under the control of the MPU along conductive leads 112. The analog switches are arranged to activate resistive voltage dividers to scale the input voltage to ranges acceptable to the MPU analog-to-digital A/D inputs 108 These signals are conveyed through a set of programmable gain amplifiers 111 under the control of the MPU along conductive leads 110.

The MPU processes the data collected into transmittable packets in a format acceptable to one of the three types of transceivers 140, 150, and 160 mounted on module 60. This data is passed along signal path 122 to a signal switch 130 to be spit into at least one bidirectional path 132, 134, and 136 connected to each transceiver. Depending on the module 60 requirements for an individual structure monitoring site, the possibility of one, two or all three transceivers will be present. A transceiver, it is understood for the purpose of this application, is a bidirectional radio frequency (RF) link capable of linking at a distance to another similar module sharing the same data exchange protocol. Each transceiver is switched to in turn to an antenna switch 170 by selection lead 124. The antenna switch 170 is couple to a multiband antenna 62 by suitable RF conductive leads 172.

Module 60 can be outfitted in several configurations to accommodate the differing distances between monitoring sites. Short range transmission using transceiver 140 allows the communication between adjacent modules 60 located along a pipeline or other protected structure. Each site can talk with a nearest neighbor and each neighbor can relay more distant data and instructions to a more remote site. Dependant on the amount of data or instructions relayed, the SRT transceiver 140 may be the only transceiver needed on the module 60. This short range link offers the economy of a non-subscription, cost-free transmission of data and instruction. Only one member of the chain is connected to a paid subscription link to a commercial carrier. Seven or more locally linked modules require only one paid subscription link.

In a second configuration of this application, a central electronic circuit module 60, in contact with nearby neighbors, is equipped with a cellular transceiver CST 150 along with the SRT 140. This central module is in RF contact with a paid subscriber based cellular tower within reception range. The CST calls up a remote station 200.

A third configuration of central electronic circuit module 60 relies upon an orbiting satellite transceiver OST module 160 to communicate data and instructions with a paid subscription, satellite based transceiver. SRT transceiver 140, also present, remains in contact with nearby neighboring modules.

Data and instructions transmitted and received through antenna 62 are relayed by external transceiver link 300, either cellular or satellite in nature, to a remote station 200. A direct wire link from a telephone central office or a wireless link communicates with module 200. RF communications are received through antenna 202 and RF cable 204 to transceiver 210 coupled to data processor 212. In turn, the data and instructions are communicated between a computer 208 by wired modem 214 and connection 206, or through wireless modem 211 and antenna 216 to antenna 218 connected with computer 208.

The fact that nearby neighbor modules communicate without the need for each module having a paid subscriptions to cellular or satellite transceivers offer great economies to this application. Several modules in a chain communicate with the central module.

Figure 4:
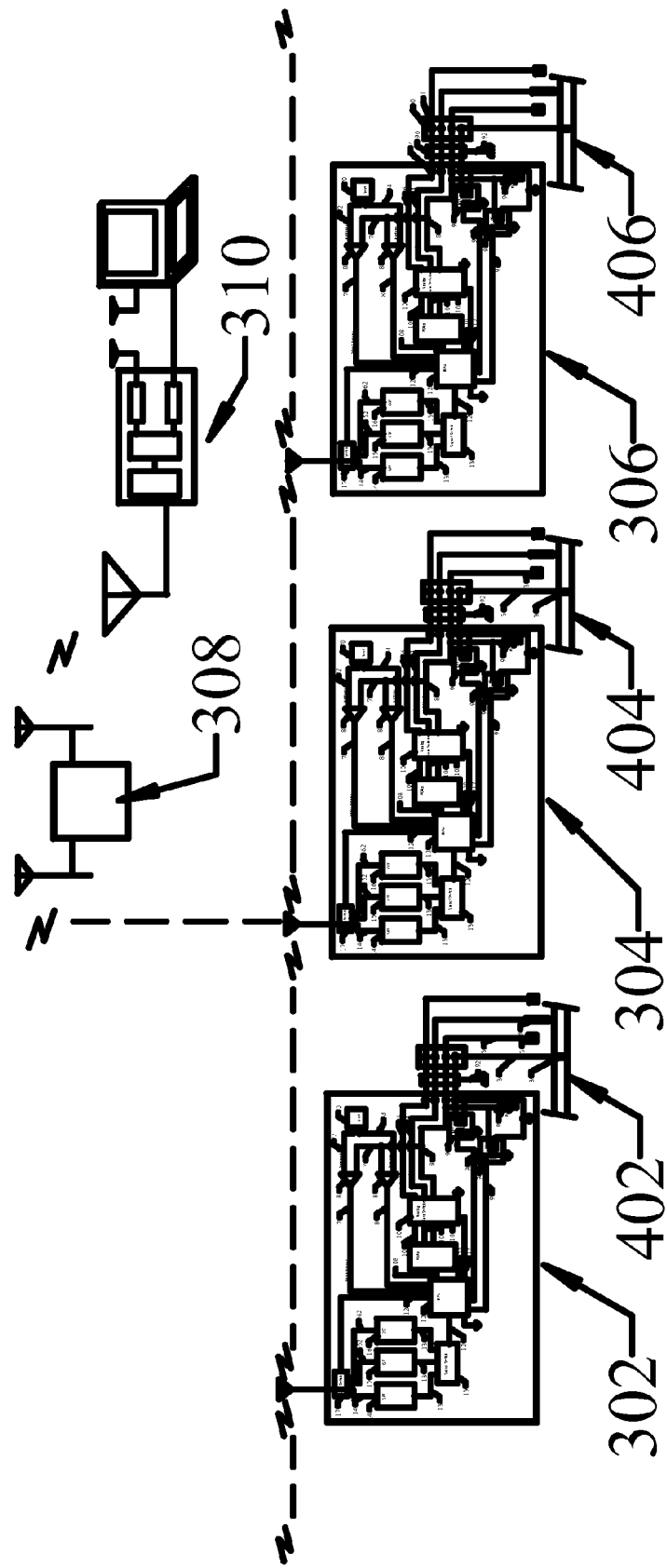
FIG. 4 is a schematic of a chain of remote modules in communication with each other having a central module in communication with a central data station.

FIG. 4 details several modules along the pipeline forming a chain of communication. Sections 402, 404 and 406 of the pipeline are equipped with peripheral modules 302 and 306 having short range transceivers only in communication with central module 304 having both a short range transceiver and a longer range transceiver in contact with relay link 308. The relay link is either a cellular service link or an orbiting satellite link. In turn, the relay link is in communication with a central station 310 where the data is recorded. The central station prepares any necessary update instructions to be sent to the pipeline modules. The modules can be remotely reprogrammed in the field. Depending upon the data management requirements of each module, the number of modules in the chain can easily exceed seven. In this manner a single cellular or satellite paid subscriber link can serve at least seven data gathering stations supervised by individual modules. This reduces the supervisory costs by a factor of seven or more.

In another embodiment of the remote monitoring apparatus, a chain of electronic modules each in radio frequency communication with the nearby neighbor module conveys pipeline corrosion protection status to a nearby neighbor module and receives updated instructions from the nearby neighbor module. The terminal electronic module at ends of the chain have a longer range transceiver and redundantly providing the longer range radio frequency link to a remote station. This configuration is useful in finding a dead link within the chain. The linkage is tested from both ends. The location of one or more non-responding links is more easily located by testing from both ends of the chain of transceivers. One of the terminal modules, longer range transceivers is only called upon if there is a dead link in the communication chain. A small amount of data transmitted and a long length of time between transmissions are expected in corrosion control. Thus, delays between transceivers and the amount of data transmitted will determine the maximum length of the chain. Reading a chain of transceivers from either end allows for a longer chain with redundant links to communicate with a distant central data collection point.

All of the embodiments will have at least one long range RF link. On a long pipeline, a linked chain will have several adjacent short-range transceiver equipped modules before encountering a module with an additional longer range transceiver. A pattern in the chain, where L is a longer range transceiver and S is a short range transceiver, will look similar to one of the chains that follow:

L-S-S-S-S-S . . . S-S-S-S-S-L or
L-S-S-S-S-L-S-S-S-S-L-S-S-S-S-L-S-S-S-S-L or
S-S-S-S-S-L-S-S-S-S-S or
L-S-S-S-S-S-S-S.

The length of the short range chain portions is determined by the data stream length and data transmission timing requirements. Short bursts at rapid rates will allow more short range transceivers between the longer range transceivers.

We claim:

1. A monitoring apparatus comprising at least one electronic module having
    at least one DC voltage measurement range;
    at least one DC current measurement range;
    at least one AC voltage measurement range;
    at least one AC current measurement range;
    a low voltage threshold trigger circuit;
    a high voltage threshold trigger circuit;
    a supervisory microprocessor unit;
    at least one analog range switching circuit under control of the supervisory microprocessor unit;
    at least one programmable gain amplifier under the control of the supervisory microprocessor unit;
    a radio frequency module selection circuit under the control of the supervisory microprocessor unit;
    at least one short range transceiver to transmit data and receive instructions to nearby neighbor module;
    an antenna switch under the control of the supervisory microprocessor unit to connect the short range transceiver to an antenna;
    wherein the at least one programmable gain amplifier remotely monitors AC and DC voltages and currents on pipelines and other metallic structures to prevent electrolytic corrosion.

2. A remote monitoring apparatus as cited in claim 1 comprising at least one electronic module having
    a relay to open a link between an active coupon and a connection to a structure;
    and
    a relay to insert a known resistor between the active coupon and the connection to the structure;
    thereby, measuring voltages and currents present on the active coupon and the structure.

3. A monitoring apparatus comprising a chain of electronic modules each having
    at least one DC voltage measurement range;
    at least one DC current measurement range;
    at least one AC voltage measurement range;
    at least one AC current measurement range;
    a low voltage threshold trigger circuit;
    a high voltage threshold trigger circuit;
    a supervisory microprocessor unit;
    at least one analog range switching circuit under control of the supervisory microprocessor unit;
    at least one programmable gain amplifier under the control of the supervisory microprocessor unit;
    a radio frequency module selection circuit under the control of the supervisory microprocessor unit;
    at least one short range transceiver to transmit data and receive instructions to nearby neighbor module;
    an antenna switch under the control of the supervisory microprocessor unit to connect the short range transceiver to an antenna;
    at least one of the electronic modules having a longer range transceiver for more distant communication with a cellular or satellite transceiver in communication with a central station;
    wherein the at least one programmable gain amplifier remotely monitors AC and DC voltages and currents on pipelines and other metallic structures at periodic distances to prevent electrolytic corrosion.

4. As cited in claim 2, a remote monitoring apparatus comprising a chain of said electronic modules each in radio frequency communication with the nearby neighbor module;
    each of the electronic modules conveying pipeline corrosion protection status to the nearby neighbor module;
    each of the electronic modules receiving updated instructions from the nearby neighbor module;
    each terminal electronic module at ends of the chain having a longer range transceiver;
    thereby, redundantly providing the longer range radio frequency link to a remote station.

5. As cited in claim 2, a remote monitoring apparatus comprising a chain of said electronic modules each in radio frequency communication with the nearby neighbor module;
    each the electronic modules conveying pipeline corrosion protection status to the nearby neighbor module;
    each of the electronic modules receiving updated instructions from the nearby neighbor module;
    each of the longer range transceiver electronic modules periodically interspersed within the chain of the short range transceiver modules;
    thereby, providing periodically placed longer range radio frequency links to a remote station.

* * * * *